US012660985B2

(12) United States Patent
Hari

(10) Patent No.: US 12,660,985 B2
(45) Date of Patent: Jun. 23, 2026

(54) ENDOSCOPE SYSTEM, ENDOSCOPE, AND CONTROL METHOD FOR ENDOSCOPE

(71) Applicant: OLYMPUS MEDICAL SYSTEMS CORP., Tokyo (JP)

(72) Inventor: Shunsuke Hari, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 459 days.

(21) Appl. No.: 18/102,096

(22) Filed: Jan. 27, 2023

(65) Prior Publication Data

US 2023/0255447 A1 Aug. 17, 2023

Related U.S. Application Data

(60) Provisional application No. 63/309,123, filed on Feb. 11, 2022.

(51) Int. Cl.
*A61B 1/00* (2006.01)
*A61B 1/045* (2006.01)

(52) U.S. Cl.
CPC ........ *A61B 1/00062* (2013.01); *A61B 1/0002* (2013.01); *A61B 1/00025* (2013.01); *A61B 1/00154* (2013.01); *A61B 1/045* (2013.01)

(58) Field of Classification Search
CPC .............. A61B 1/0002; A61B 1/00025; A61B 1/00062; A61B 1/00154; A61B 1/045; A61B 1/05
See application file for complete search history.

(56) References Cited

U.S. PATENT DOCUMENTS

| | | | | |
|---|---|---|---|---|
| 2001/0051766 A1* | 12/2001 | Gazdzinski | ............ | A61B 10/02 606/1 |
| 2002/0188173 A1* | 12/2002 | Kobayashi | ......... | A61B 1/00062 600/118 |
| 2003/0135091 A1* | 7/2003 | Nakazawa | ......... | A61B 1/00154 600/101 |
| 2004/0165846 A1* | 8/2004 | Ota | .......................... | A61B 1/05 348/E7.087 |
| 2004/0176683 A1 | 9/2004 | Whitin et al. | | |
| 2009/0253967 A1* | 10/2009 | Gill | .................... | A61B 1/00059 600/249 |
| 2010/0113877 A1* | 5/2010 | Suzuki | ............... | A61B 1/00059 600/117 |
| 2017/0086906 A1* | 3/2017 | Tsuruta | .................. | A61B 1/051 |
| 2020/0297183 A1* | 9/2020 | Lohier | ............... | A61B 1/00062 |
| 2022/0167837 A1 | 6/2022 | Onikubo et al. | | |

FOREIGN PATENT DOCUMENTS

| | | |
|---|---|---|
| JP | 2009-240405 A | 10/2009 |
| JP | 2011-177382 A | 9/2011 |
| JP | 2012-005857 A | 1/2012 |
| JP | 2016-007275 A | 1/2016 |
| JP | 2020-156814 A | 10/2020 |

* cited by examiner

*Primary Examiner* — Aaron B Fairchild
(74) *Attorney, Agent, or Firm* — Morgan, Lewis & Bockius LLP

(57) ABSTRACT

An endoscope system includes a controller configured to receive a detection result relating to insertion of an insertion section of an endoscope into a subject, and record information indicating use of the endoscope based on the detection result in the memory.

18 Claims, 11 Drawing Sheets

ENDOSCOPE SYSTEM, ENDOSCOPE, AND CONTROL METHOD FOR ENDOSCOPE

RELATED APPLICATION DATA

This application is based on and claims priority under 35 U.S.C. § 119 to U.S. Provisional Application No. 63/309,123 filed on Feb. 11, 2022, the entire contents of which are incorporated herein by reference.

FIELD OF DISCLOSURE

The present disclosure relates to an endoscope system and an endoscope including an insertion section to be inserted into a subject and a control method for the endoscope.

BACKGROUND

An endoscope is used to observe an inside of a subject and includes an insertion section to be inserted into the subject. As the endoscope, there are a reusable endoscope used a plurality of times by performing reprocessing and a single-use endoscope used only once.

Since the single-use endoscope is packed in a sterilized package and shipped in a state in which sterilization is maintained, the single-use endoscope can be used when the sterilized package is opened. The single-use endoscope is discarded when used only once and does not need to be subjected to reprocessing.

There has been proposed a technique for preventing a used single-use endoscope from being used by mistake. For example, Japanese Patent Application Laid-Open Publication No. 2011-177382 describes an endoscope system including a sensor that detects presence or absence of use of an endoscope, a cover that covers the sensor, and a memory that stores information concerning the presence or absence of use of the endoscope. When electrically detecting that the cover is removed in a state in which a power supply of the endoscope is on, the endoscope system sets a "used" bit in the memory at the time of use approval by an operator or at the time of timer over to disable reuse of the endoscope.

SUMMARY OF THE DISCLOSURE

An endoscope system according to an aspect of the present disclosure includes a controller configured to receive a detection result relating to insertion of an insertion section of an endoscope into a subject, and record information indicating use of the endoscope based on the detection result in the memory.

An endoscope according to an aspect of the present disclosure includes an insertion section insertable into a subject, a sensor configured to detect a detection result relating to insertion of the insertion section into the subject, a memory, and a controller. The controller is configured to receive the detected detection result, and record information indicating concerning the detected detection result in the memory.

A control method for an endoscope including an insertion section insertable into a subject according to an aspect of the present disclosure is a control method for an endoscope comprising receiving a detection result relating to insertion of the insertion section into the subject, and recording information indicating concerning the detection result in a memory.

DETAILED DESCRIPTION

Figure 1:
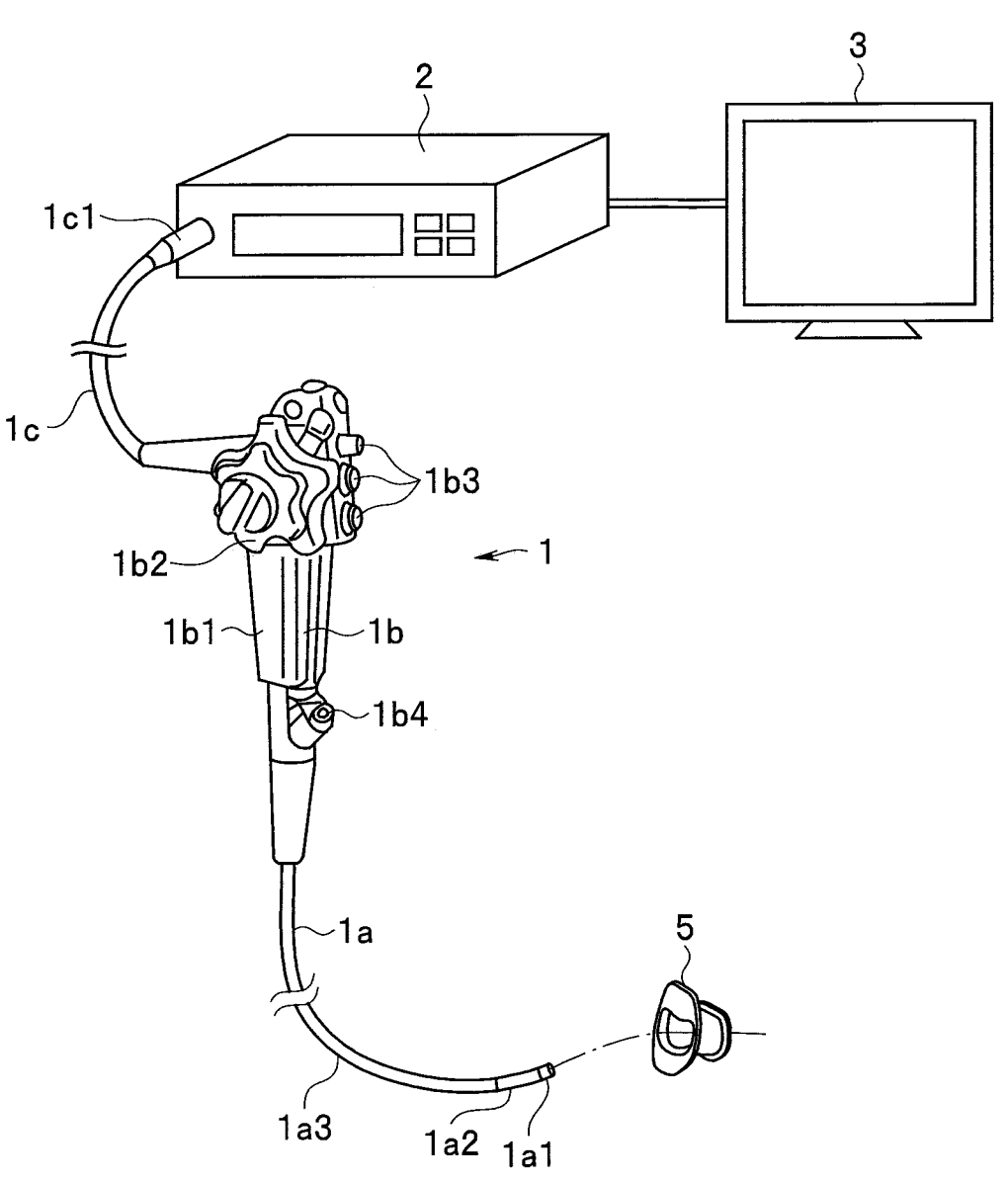
FIG. 1 is a perspective view showing a configuration of an endoscope system in a first embodiment of the present disclosure.

In general, in the technique described in Japanese Patent Application Laid-Open Publication No. 2011-177382, the cover needs to be removed before an endoscopic examination is performed. Work for removing the cover is a burden on a user.

According to embodiments explained below, it is possible to provide an endoscope system, an endoscope, and a control method for the endoscope that can reduce a burden on a user and prevent reuse.

Embodiments of the present disclosure are explained below with reference to the drawings. However, the present disclosure is not limited by the embodiments explained below.

Note that, in description of the drawings, the same or corresponding elements are denoted by the same reference numerals and signs as appropriate. The drawings are schematic. It needs to be noted that, in one drawing, relations among lengths of respective elements, ratios of the lengths of the respective elements, quantities of the respective elements, and the like are sometimes different from real ones in order to simplify explanation. Further, among a plurality of drawings, portions having different relations and ratios of lengths in the drawings are sometimes included.

First Embodiment

FIG. 1 to FIG. 5 show a first embodiment of the present disclosure. FIG. 1 is a perspective view showing a configuration of an endoscope system in the first embodiment. FIG.

2 is a block diagram mainly showing an electric configuration of the endoscope system in the first embodiment.

Figure 2:
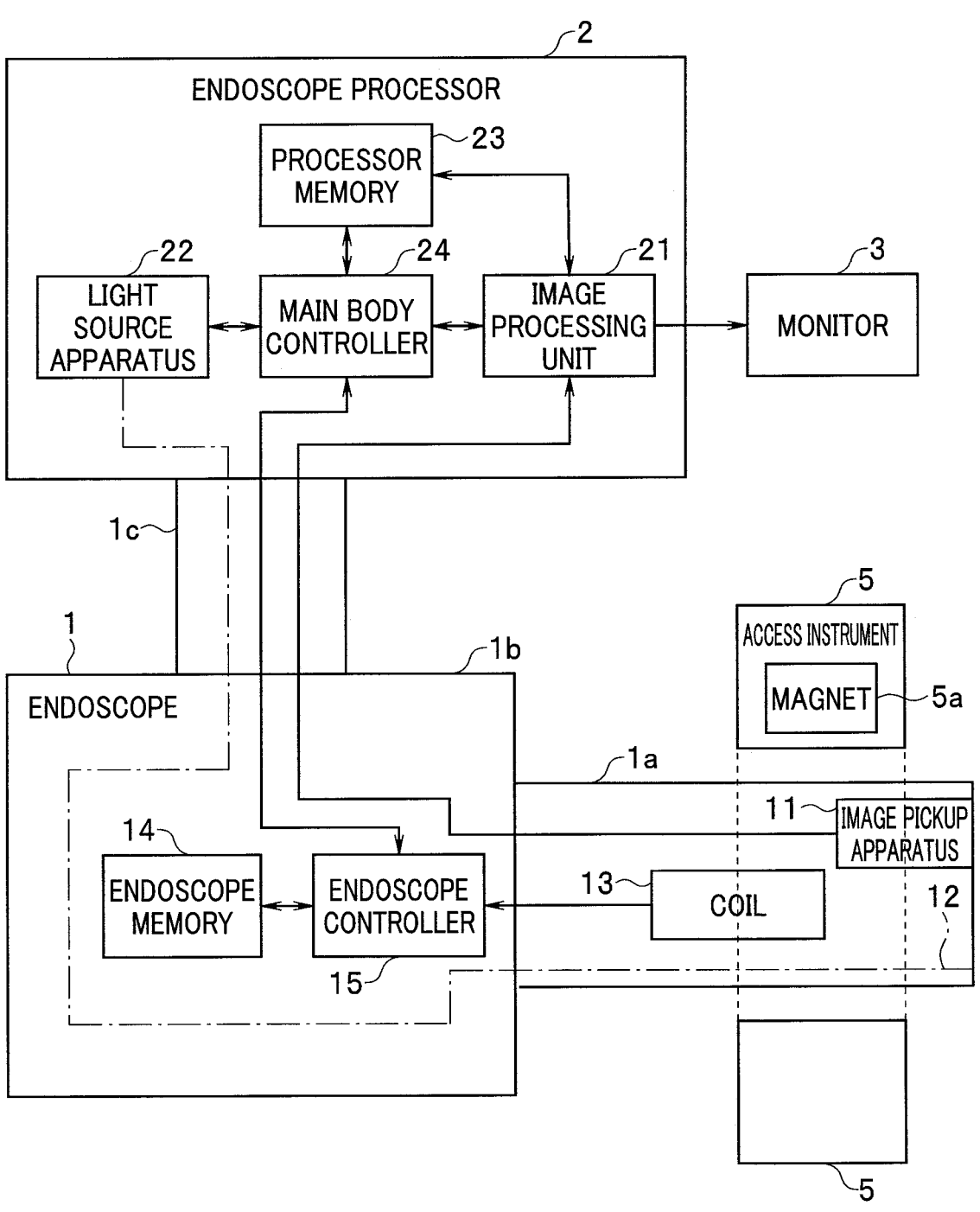
FIG. 2 is a block diagram mainly showing an electric configuration of the endoscope system in the first embodiment.

As shown in FIG. 1 and FIG. 2, the endoscope system includes an endoscope 1, an endoscope processor 2, a monitor 3, and an access instrument 5.

The endoscope 1 is configured as a single-use endoscope that is discarded when used only once. Note that, here, a case in which the endoscope 1 is the single-use endoscope is explained as an example. However, the endoscope 1 may be a reusable endoscope. The reusable endoscope is a rent endoscope and is an endoscope of a type that is collected by a manufacturer or a trader when used once and reprocessed by the manufacturer or the like. When the reprocess is performed on the manufacturer side, a "used" flag recorded in an endoscope memory 14 explained below is reset. Since the endoscope memory 14 is not reset (cannot be reset) until the reprocess is performed on the manufacturer side, the endoscope 1 is prohibited from being continuously used for a second time on a user side. The endoscope 1 includes an insertion section 1a, an operation section 1b, and a universal cord 1c.

The insertion section 1a is a part to be inserted into a subject. Note that a subject into which the insertion section 1a maintained in sterilization is inserted is assumed to be an organism such as a human body or an animal.

The insertion section 1a includes a distal end portion 1a1, a bending section 1a2, and a flexible tube section 1a3 in order from a distal end side toward a proximal end side.

The endoscope 1 is configured as, for example, an electronic endoscope. An image pickup apparatus 11 (see FIG. 2) that picks up an image of the subject is provided in the distal end portion 1a1. The image pickup apparatus 11 includes an objective optical system and an image pickup device (an image sensor). The objective optical system forms an optical image. The image pickup device photoelectrically converts the formed optical image and outputs an image pickup signal.

A signal line connected to the image pickup apparatus 11, a light guide 12 (see FIG. 2) that transmits illumination light, a bending wire for bending the bending section 1a2, a treatment instrument channel for allowing insertion of a treatment instrument for endoscope, and the like are disposed in the insertion section 1a.

Further, a coil 13 is provided in the insertion section 1a as a sensor that acquires a result of detecting that the insertion section 1a has been inserted into the access instrument 5. The coil 13 is connected to an endoscope controller 15 (see FIG. 2) explained blow and functions as a magnetic sensor. Note that a setting place of the coil 13 is not particularly limited if the setting place is in the insertion section 1a. However, for example, if the coil 13 is provided in a position of approximately 20 to 30 cm from a distal end face of the insertion section 1a, it is surely detected that the distal end portion 1a1 has passed through the access instrument 5 and has been inserted into the subject. The access instrument 5 is configured to guide the insertion section 1a into the subject. The endoscope 1 includes a sensor 13 configured to acquire or detect the detection result when the insertion section 1a is inserted into the access instrument 5. The access instrument 5 includes a magnetic material configured to generate a magnetic field. The sensor includes the coil 13, and the detection result is an electric current in the coil 13 occurring when the magnetic material moves relative to the coil 13 during inserting of the insertion section 1a into the access instrument 5.

An illumination window on a distal end side of the light guide 12, an observation window on the distal end side of the objective optical system, and a distal end side opening of the treatment instrument channel are disposed on a distal end face of the distal end portion 1a1.

The bending section 1a2 is a bendable part disposed on a proximal end side of the distal end portion 1a1. The bending section 1a2 is configured to be bendable in, for example, two directions or upward, downward, left, and right four directions.

When the bending section 1a2 is bent, a direction of the distal end portion 1a1 changes and an observation direction of the image pickup apparatus 11 and a radiation direction of illumination light from the light guide 12 change. The bending section 1a2 is also bent for improving insertability of the insertion section 1a in the subject.

The flexible tube section 1a3 is a tube section disposed on the proximal end side of the bending section 1a2 and having flexibility. Note that, here, a soft endoscope including the flexible tube section 1a3 is explained as an example of the endoscope 1. However, the endoscope 1 may be a rigid endoscope in which a portion corresponding to the flexible tube section 1a3 is rigid.

The operation section 1b is a part disposed on the proximal end side of the insertion section 1a and for operating the endoscope 1. The operation section 1b includes a grasping section 1b1, a bending operation knob 1b2, a plurality of operation buttons 1b3, and a treatment instrument insertion port 1b4.

The grasping section 1b1 is a part where an operator grasps the endoscope 1 with a hand.

A bending operation knob 1b2 is an operation device for operating bending of the bending section 1a2 using, for example, a thumb of a hand grasping the grasping section 1b1. When the bending operation knob 1b2 is operated, the bending wire is towed and the bending section 1a2 is bent.

The plurality of operation buttons 1b3 include, for example, an air feeding and liquid feeding button, a suction button, and a button relating to image pickup. The air feeding and liquid feeding button is a button for operation for feeding air and liquid to the observation window of the distal end portion 1a1 through a not-shown air feeding and liquid feeding channel and cleaning the observation window. The suction button is a button for operation for suctioning liquid, a mucous membrane, and the like from an inside of the subject through, for example, the treatment instrument channel also functioning as a suction channel. The button relating to image pickup is, for example, a button switch for release operation.

The treatment instrument insertion port 1b4 is an opening on the proximal end side of the treatment instrument channel. Various treatment instruments such as forceps are inserted into the treatment instrument channel through the treatment instrument insertion port 1b4. A distal end portion of a treatment instrument projects from the distal end side opening of the treatment instrument channel provided at the distal end portion 1a1 and performs various treatments.

As shown in FIG. 2, an endoscope memory 14 and an endoscope controller 15 are further provided in, for example, the operation section 1b of the endoscope 1. Note that, in FIG. 2, an example is shown in which the endoscope memory 14 and the endoscope controller 15 are provided in the operation section 1b. However, the endoscope memory 14 and the endoscope controller 15 may be provided in, for example, a connector 1c1. Regardless of these, disposition of the endoscope memory 14 and the endoscope controller 15 is not limited if the endoscope memory 14 and the endoscope controller 15 are provided in the endoscope 1.

The endoscope memory 14 includes a nonvolatile memory and stores, in a nonvolatile manner, history information indicating whether the endoscope 1 is unused or used. The information may be represented by, for example, a one-bit "used" flag. In this case, the information indicates that the endoscope 1 is unused when a bit value is "0" (the "used" flag is not set) and indicates that the endoscope 1 is used when the bit value is "1" (the "used" flag is set). Note that the "used" flag may be configured not to be rewritten after the bit value changes from "0" to "1".

The endoscope controller 15 determines, based on an output from the coil 13, whether the access instrument 5 has been detected and, when the access instrument 5 has been detected, determines that the endoscope 1 is used and rewrites the "used" flag of the endoscope memory 14 to "1".

In other words, in the present embodiment, as an event relating to insertion of the insertion section 1a into the subject, an event in which the access instrument 5 has been detected (more specifically, as explained below, an event in which an electric current flowing from the coil 13 has been detected because the coil 13 has moved relative to a magnet 5a) is used. As information concerning a detection result recorded in the endoscope memory 14, the history information (the "used" flag) indicating whether the endoscope 1 is unused or used is used. The endoscope controller 15 is configured to receive the detection result relating to insertion of the insertion section 1a of the endoscope 1 into the subject, and record the information indicating use of the endoscope 1 based on the detection result. The controller 15 is further configured to determine whether the information indicating use of the endoscope 1 is recorded in the endoscope memory 14, permit operation of the endoscope 1 when the information is not recorded, and prevent operation of the endoscope 1 when the information is recorded. The endoscope memory 14 is configured to store the detection result. A processor memory 23, and a main body controller 24 may be used as alternative of the endoscope controller 15 and the endoscope memory 14 respectively.

One end of the universal cord 1c is connected to, for example, a side surface on the proximal end side of the operation section 1b. A connector 1c1 connected to the endoscope processor 2 is provided at the other end of the universal cord 1c. The signal line and the light guide 12 extended from the insertion section 1a through the operation section 1b, a suction channel communicating with the treatment instrument channel, and the like are disposed in the universal cord 1c.

The endoscope processor 2 is a processor to which the endoscope 1 is connected, the processor performing processing relating to the endoscope 1. As shown in FIG. 2, the endoscope processor 2 includes an image processing unit 21, a light source apparatus 22, a processor memory 23, and a main body controller 24. Note that, here, an example is explained in which the endoscope processor 2 includes the light source apparatus 22. However, the light source apparatus 22 may be configured separately from the endoscope processor 2.

The image processing unit 21 receives an image pickup signal from the image pickup apparatus 11 through the signal line. The image processing unit 21 is an image processing apparatus that performs various kinds of image processing such as demosaicking, noise correction, color correction, contrast correction, and gamma correction on the image pickup signal and generates a displayable image signal. The image processing unit 21 may superimpose various kinds of information such as character information and guide information on the image signal.

Note that the main body controller 24 and the image processing unit 21 of the endoscope processor 2 may be configured to perform functions of the respective units by a processor such as an ASIC (application specific integrated circuit) or an FPGA (field programmable gate array) including a CPU (central processing unit) reading and executing a processing program recorded in the processor memory 23, which is a recording apparatus. At least a part of the endoscope processor 2 may be configured as a dedicated electronic circuit.

The light source apparatus 22 includes a light source that emits illumination light. Note that, here, an example of an illumination apparatus that transmits, with the light guide 12, the illumination light emitted by the light source apparatus 22 and radiates the illumination light from the insertion section 1a is explained. However, the illumination apparatus may be an illumination apparatus in which a light emitting element such as an LED is provided at the distal end portion 1a1 of the insertion section 1a instead of the light guide 12, the illumination apparatus supplying an electric current to the light emitting element to emit the illumination light and radiating the illumination light.

The processor memory 23 records a processing program to be executed by the main body controller 24, various parameters used for processing, setting values by the user, an image signal to be processed by the image processing unit 21, and the like. As information to be recorded, there are information that only has to be temporarily recorded such as an image signal and information that needs to be continuously recorded such as a processing program. Therefore, the processor memory 23 may include a volatile memory and a nonvolatile memory.

The main body controller 24 controls the respective units in the endoscope processor 2 including the image processing unit 21 and the light source apparatus 22 and reads out information from and writes information in the processor memory 23. Further, the main body controller 24 is connected to the endoscope controller 15 and controls the endoscope 1 through the endoscope controller 15.

The monitor 3 is connected to the endoscope processor 2 and displays an image relating to the image signal processed by the image processing unit 21.

The access instrument 5 is an instrument used in inserting the insertion section 1a of the endoscope 1 into the subject. When an endoscopic examination is started, the insertion section 1a is inserted into the access instrument 5. The insertion section 1a is inserted into the subject through the access instrument 5. Several examples of the access instrument 5 include a mouthpiece and a trocar. However, the access instrument 5 is not limited to the mouthpiece and the trocar. The access instrument 5 in the present embodiment includes the magnet 5a, which is a magnetic body that generates a magnetic field.

Figure 3:
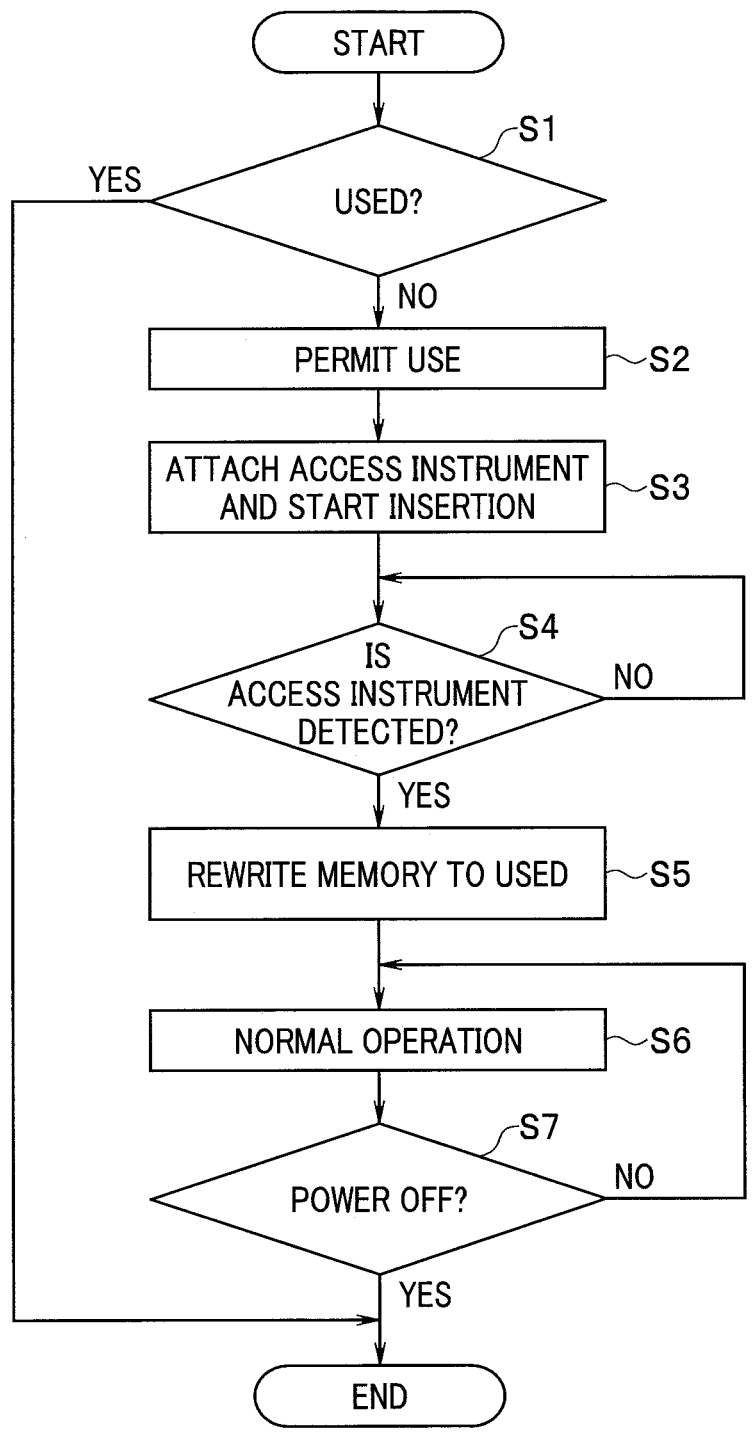
FIG. 3 is a flowchart showing a first example of action of the endoscope system in the first embodiment.

FIG. 3 is a flowchart showing a first example of action of the endoscope system in the first embodiment.

When the connector 1c1 is connected to the endoscope processor 2, the light guide 12 and the signal line are connected to the endoscope processor 2.

When a power supply of the endoscope 1 is turned on and power supply from the endoscope processor 2 to the endoscope 1 is started, the endoscope controller 15 reads out the "used" flag recorded in the endoscope memory 14 and, when the bit value of the "used" flag is "0", determines that the endoscope 1 is unused and, when the bit value is "1", determines that the endoscope 1 is used (step S1).

When it is determined here that the endoscope 1 is used, the endoscope controller 15 prohibits use of the endoscope 1 and ends operation of the endoscope 1. Note that when the endoscope 1 is used, before ending the operation of the endoscope 1, the endoscope controller 15 may transmit indication that the endoscope 1 is used to the main body controller 24. The main body controller 24 may display "end the processing because the endoscope is used" or the like on the monitor 3 to cause the user to recognize that the endoscope 1 is used.

When it is determined in step S1 that the endoscope 1 is not used but is unused, the endoscope controller 15 permits the use of the endoscope 1 and starts the operation of the endoscope 1 (step S2). Then, the light source apparatus 22 supplies illumination light to the light guide 12 of the endoscope 1. The light guide 12 transmits the illumination light and radiates the illumination light from the illumination window of the distal end portion 1a1 toward the subject. The illumination light radiated from the illumination window is reflected by the subject to be return light.

The endoscope processor 2 transmits a driving signal and electric power to the image pickup apparatus 11. The image pickup apparatus 11 picks up an optical image of the subject according to the driving signal and generates an image pickup signal. The image pickup by the image pickup apparatus 11 is sequentially performed, for example, in frame units and an image pickup signal relating to moving images of a plurality of frames is generated. The image pickup signal is transmitted to the endoscope processor 2 through the signal line.

The endoscope processor 2 receives the image pickup signal, performs the image processing as explained above, and generates a displayable image signal. The image signal generated by the endoscope processor 2 is outputted to the monitor 3. The monitor 3 displays an image based on the image signal. In this way, the image can be displayed according to the use permission in step S2.

The user attaches the access instrument 5 to the subject and starts inserting the insertion section 1a into the subject through the access instrument 5 (step S3).

When the insertion section 1a passes through the access instrument 5, the magnetic field of the magnet 5a piercing through the coil 13 changes according to relative movements of the coil 13 and the magnet 5a and an induction current is generated in the coil 13 by electromagnetic induction. The endoscope controller 15 monitors the induction current flowing from the coil 13 and determines, for example, according to whether an induction current value has exceeded a predetermined current threshold, whether the access instrument 5 has been detected (step S4).

Here, the endoscope controller 15 stays on standby until the access instrument 5 is detected and, when the access instrument 5 is detected, rewrites the "used" flag of the endoscope memory 14 to a state in which the endoscope 1 is used (step S5).

Subsequently, the endoscope controller 15 performs a normal operation of the endoscope 1 (step S6). In other words, even if the "used" flag is set, the endoscope 1 can be continuously used while the power supply of the endoscope 1 is on.

Thereafter, the endoscope controller 15 determines whether the power supply is off (step S7) and returns to step S6 and continuously performs the normal operation until it is determined that the power supply is off.

When it is determined in step S7 that the power supply is off in this way, the endoscope 1 ends the operation.

Even if the endoscope 1 that has ended the operation once in this way is connected to the endoscope processor 2 again, at a restart time, it is determined in step S1 that the endoscope 1 is used, use is prohibited, and the operation is automatically ended. Therefore, the endoscope 1 is not used again.

Figure 4:
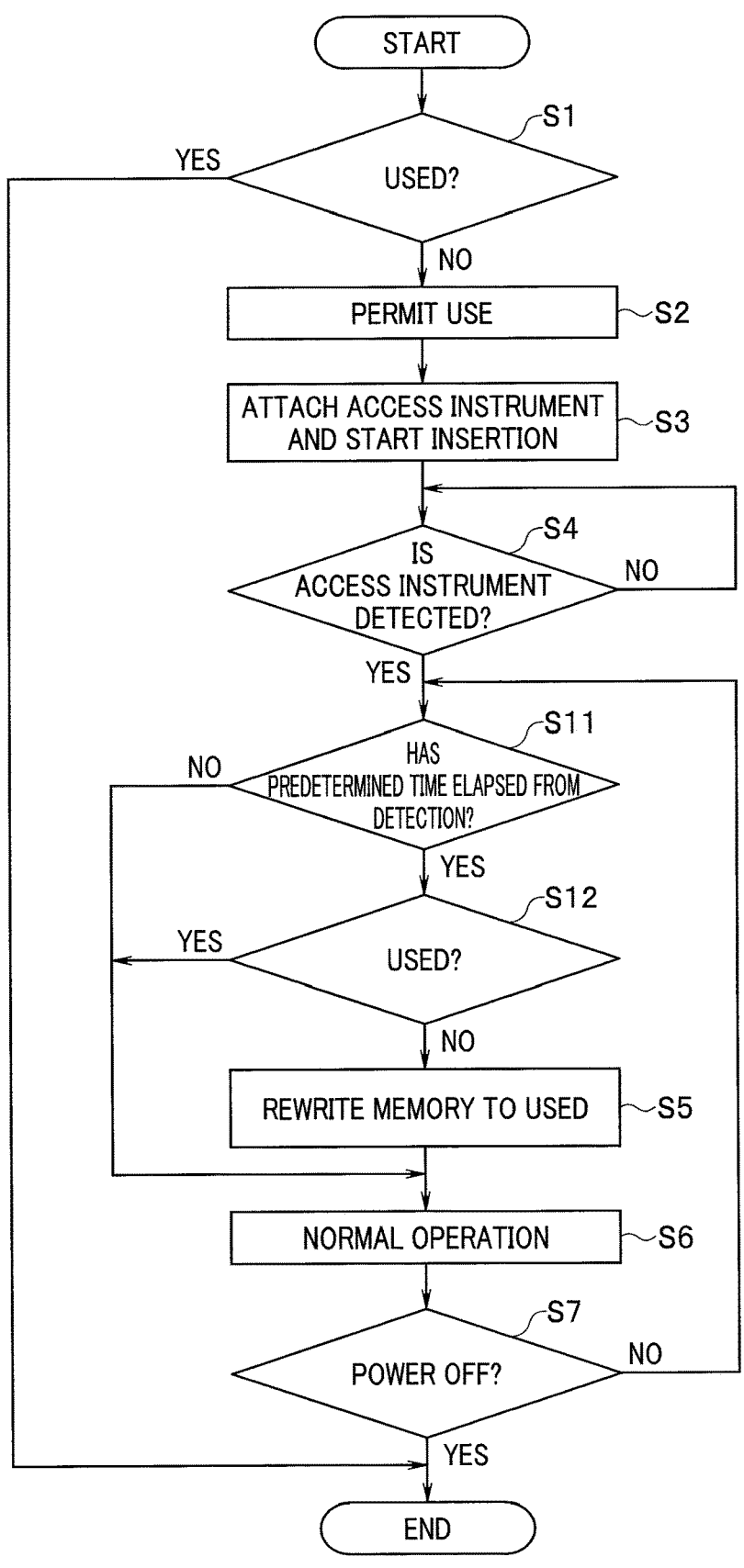
FIG. 4 is a flowchart showing a second example of the action of the endoscope system in the first embodiment.

FIG. 4 is a flowchart showing a second example of the action of the endoscope system in the first embodiment.

When starting processing shown in FIG. 4, the endoscope controller 15 performs the processing in steps S1 to S4 explained above. When the access instrument 5 is detected in step S4, the endoscope controller 15 starts a timer included in the endoscope controller 15 and determines whether a predetermined time has elapsed after the access instrument 5 was detected (step S11). When it is determined here that the predetermined time has not elapsed, the endoscope controller 15 performs the normal operation in step S6. When it is determined in step S7 that the power supply is not off, the endoscope controller 15 shifts the processing to the determination in step S11. The controller is configured to count time after receiving the detection result, and record information indicating use of the endoscope 1 when the counted time is larger than the predetermined time.

In this way, when it is determined in step S11 that the predetermined time has elapsed, the endoscope controller 15 determines whether the "used" flag of the endoscope memory 14 is set (step S12). When it is determined here that the "used" flag is set, since it may not rewrite the endoscope memory 14, the endoscope controller 15 performs the normal operation in step S6.

On the other hand, when it is determined in step S12 that the "used" flag is not set, the endoscope controller 15 performs the processing in step S5 and rewrites the "used" flag of the endoscope memory 14 to the state in which the endoscope 1 is used.

Thereafter, the endoscope controller 15 performs the normal operation in step S6. As in the processing shown in FIG. 3, the endoscope 1 ends the operation when it is determined in step S7 that the power supply is off.

In the processing shown in FIG. 3, when the power supply of the endoscope 1 is turned off by mistake during the endoscopic examination, thereafter, the endoscope 1 cannot be used even if the endoscope 1 is restarted. In contrast, in the processing shown in FIG. 4, since the endoscope memory 14 is not rewritten until the predetermined time elapses even if the access instrument 5 is detected, within the predetermined time, the endoscope 1 can be restarted even if the endoscope 1 is turned off by mistake. Therefore, for example, a time shorter than a minimum time for one endoscopic examination may be set as the predetermined time.

Note that, in the above explanation, the timer for counting the predetermined time is started at a point in time when the access instrument 5 has been detected. However, instead, the timer may be started at a point in time when the power supply of the endoscope 1 has been turned on.

Figure 5:
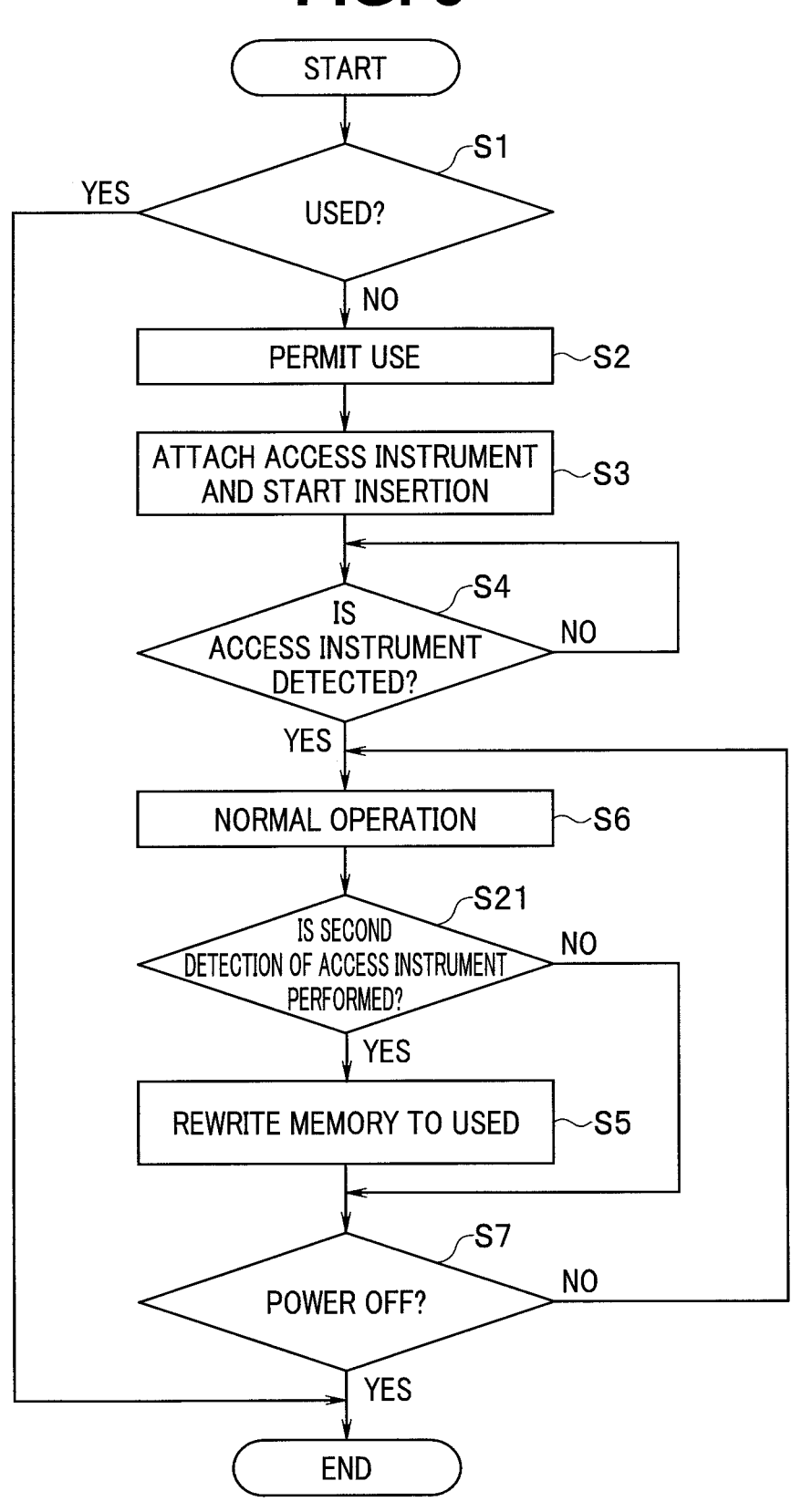
FIG. 5 is a flowchart showing a third example of the action of the endoscope system in the first embodiment.

FIG. 5 is a flowchart showing a third example of the action of the endoscope system in the first embodiment.

When starting processing shown in FIG. 5, the endoscope controller 15 performs the processing in steps S1 to S4 explained above and further performs the normal operation in step S6.

At every appropriate timing during the normal operation, the endoscope controller 15 determines whether second detection of the access instrument 5 has been performed (step S21). In other words, the endoscope controller 15 performs first detection of the access instrument 5 in step S4 when the insertion section 1a is inserted into the subject and performs second detection of the access instrument 5 in step S21 when the insertion section 1*a* is pulled out from the subject.

When it is determined that the second detection of the access instrument 5 has not been performed, the endoscope controller 15 performs the power off determination in step S7 and continuously performs the normal operation in step S6 when the power supply is not off.

When it is determined in step S21 that the second detection of the access instrument 5 has been performed, the endoscope controller 15 performs the processing in step S5 and rewrites the "used" flag of the endoscope memory 14 to the state in which the endoscope 1 is used.

Thereafter, as in the processing shown in FIG. 3 and FIG. 4, the endoscope 1 ends the operation when it is determined in step S7 that the power supply is off.

In the processing shown in FIG. 5, since the endoscope memory 14 is not rewritten until the access instrument 5 is detected twice, even if the endoscope 1 is turned off by mistake during the endoscopic examination, the endoscope 1 can be restarted as long as the insertion section 1*a* is not pulled out from the subject. The endoscope controller 15 is configured to record information indicating use of the endoscope based on the detection result received in the memory when the detection result is received twice.

Note that, in the above explanation, an example is explained in which the endoscope memory 14 is rewritten by the control of the endoscope controller 15. However, instead of this, the endoscope memory 14 may be rewritten by control of the main body controller 24 of the endoscope processor 2. In this case, the main body controller 24 may acquire an output of the coil 13 through the endoscope controller 15. When the connector 1*c*1 is connected to the endoscope processor 2, the coil 13 and the main body controller 24 may be electrically connected to enable the main body controller 24 to directly acquire the output of the coil 13.

In the above explanation, the memory that records the "used" flag is the endoscope memory 14 provided in the endoscope 1. However, the memory is not limited to this. For example, a memory may be provided on an outside of the endoscope 1 and the "used" flag may be recorded in a database in the memory to be linked with a specific value (a serial number or the like) for identifying an individual endoscope 1.

An example of the external memory in which the database is constructed may be any of the processor memory 23, a memory of a server in an in-hospital system, a memory of a server of a manufacturer connected to the endoscope processor 2 or the in-hospital system, and the like and is not particularly limited. Consequently, an individual endoscope 1 in which the "used" flag is already set as a result of referring to the database can be prevented from being restarted.

Further, in the above explanation, the "used" flag is explained as an example of the information concerning the detection result recorded in the endoscope memory 14. However, the information is not limited to this. For example, a maximum value of the induction current flowing from the coil 13 may be recorded, information indicating that the induction current value has exceeded the predetermined current threshold may be recorded, or other information may be used if it is possible to determine whether the endoscope 1 is unused or used.

According to such a first embodiment, since the controller (the endoscope controller 15 or the main body controller 24) detects the induction current generated in the coil 13 by the movement relative to the magnet 5*a* to determine whether the endoscope 1 is used, the work for removing the cover or the like before performing the endoscopic examination in the related art may not be performed. Therefore, it is possible to reduce a burden on the user and prevent reuse of the endoscope 1. It is possible to prevent, for example, the user from inserting the endoscope 1 into the subject while forgetting to remove the cover or the like. The cover does not fall in the subject.

Since history information of the "used" flag or the like is recorded in the endoscope memory 14, after it is determined that the endoscope 1 is used, the endoscope 1 is unusable even if the endoscope 1 is restarted.

At this time, by using the endoscope memory 14 provided in the endoscope 1 as a memory that records the history information, the endoscope 1 and the history information can be surely linked.

Since the coil 13 can detect the magnetic field of the magnet 5*a* in a noncontact manner, the magnetic field can be detected even if a certain degree of a blocking object is present. There is an advantage that the configuration of the first embodiment is stain-resistant.

Second Embodiment

Figure 6:
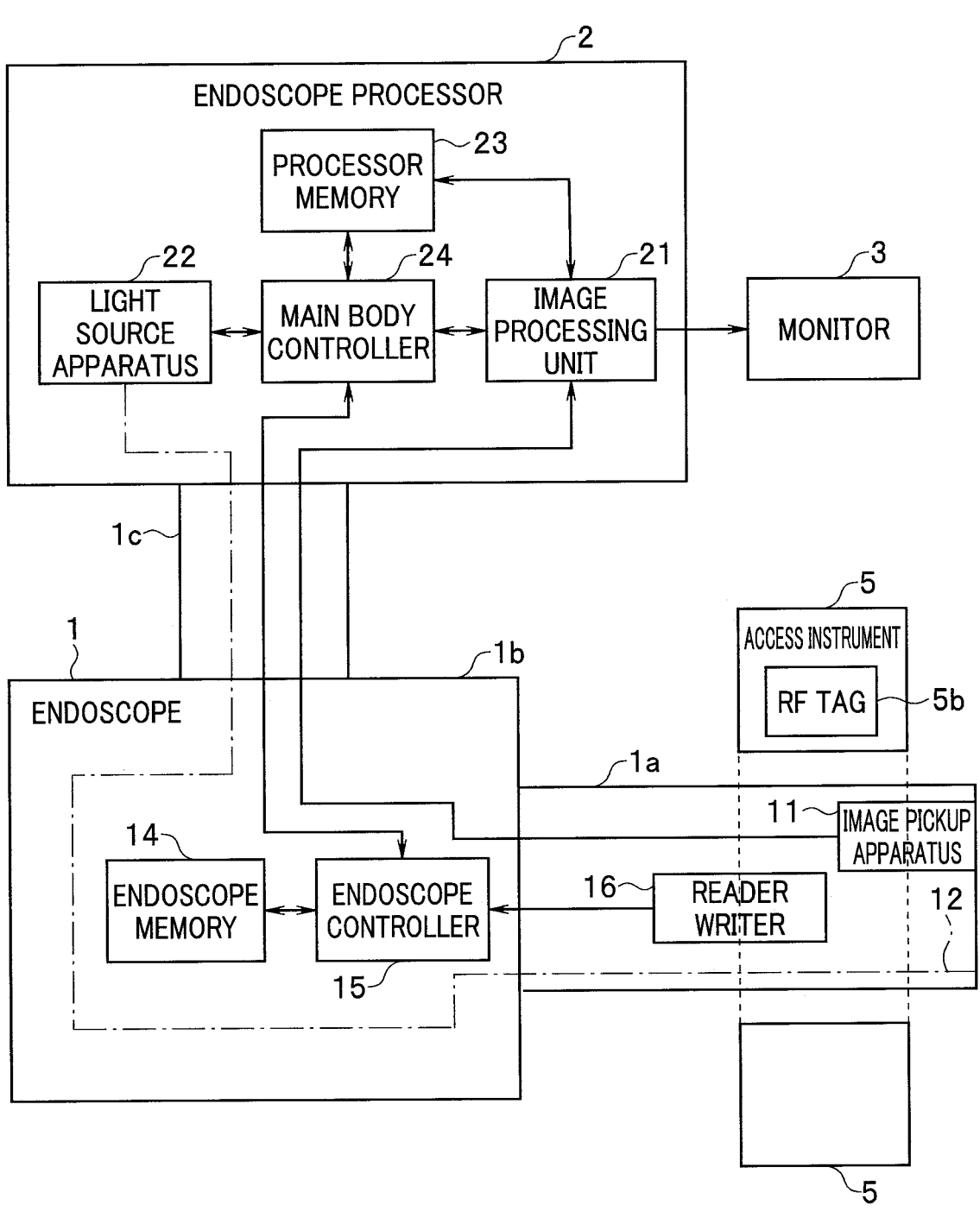
FIG. 6 is a block diagram mainly showing an electric configuration of an endoscope system in a second embodiment of the present disclosure.
Figure 7:
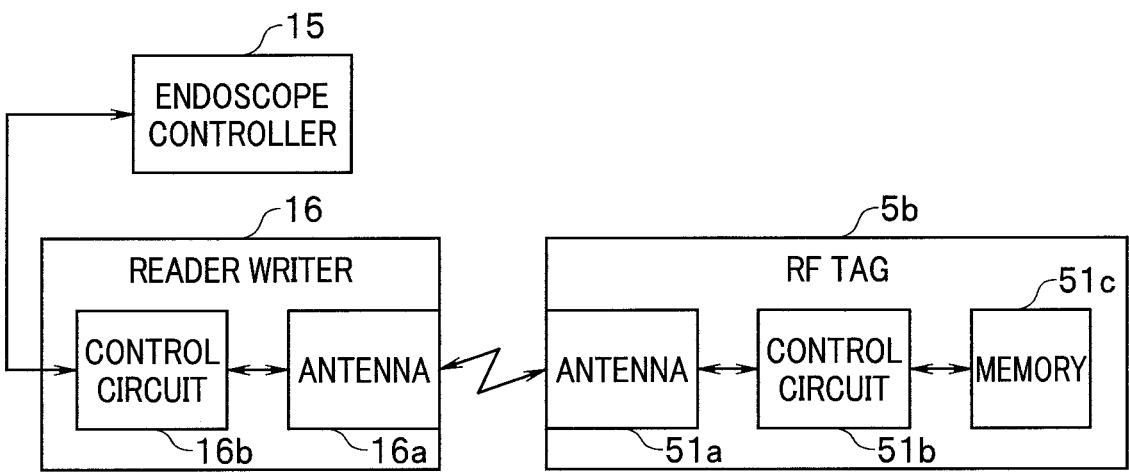
FIG. 7 is a block diagram showing configurations of a reader writer and an RF tag in the endoscope system in the second embodiment.

FIG. 6 and FIG. 7 show a second embodiment of the present disclosure. FIG. 6 is a block diagram mainly showing an electric configuration of an endoscope system in the second embodiment. In the second embodiment, the same portions as the portions in the first embodiment are denoted by the same reference numerals and signs and explanation of the portions is omitted as appropriate. Differences from the first embodiment are mainly explained.

In the first embodiment, the event relating to the insertion of the insertion section 1*a* into the subject is detected using the magnet 5*a* and the coil 13. In contrast, in the second embodiment, the event relating to the insertion of the insertion section 1*a* into the subject is detected using an RF tag 5*b* and a reader writer 16. Note that the RF tag 5*b* is called RFID tag or IC tag as well.

In other words, the RF tag 5*b* is provided in the access instrument 5. The reader writer 16 is provided in the insertion section 1*a* of the endoscope 1 as a sensor that acquires a result of detecting that the insertion section 1*a* has been inserted into the access instrument 5. A setting place of the reader writer 16 is not particularly limited if the setting place is in the insertion section 1*a*. For example, like the coil 13 in the first embodiment, the reader writer 16 may be provided in a position of approximately 20 to 30 cm from the distal end face of the insertion section 1*a*. The other components of the endoscope system are substantially the same as the components shown in FIG. 2.

FIG. 7 is a block diagram showing configurations of the reader writer 16 and the RF tag 5*b* in the endoscope system in the second embodiment.

The RF tag 5*b* includes an antenna 51*a* (a first antenna), a control circuit 51*b*, and a memory 51*c*. The reader writer 16 includes an antenna 16*a* (a second antenna) and a control circuit 16*b*. The control circuit 16*b* is connected to the endoscope controller 15.

The reader writer 16 and the RF tag 5*b* configuring RFID (radio frequency identification) may be a reader writer and an RF tag that use either an electromagnetic induction scheme or a radio wave scheme.

In the case of the electromagnetic induction scheme, a coil-type antenna is used as the antenna 16*a* and the antenna 51*a*, electric power is supplied from the reader writer 16 to the RF tag 5*b* using a magnetic field, and data is transferred from the RF tag 5*b* to the reader writer 16. Since magnetic field intensity is deteriorated at an inverse of a square of a distance, the electromagnetic induction scheme is suitable for short distance communication.

In the case of the radio wave scheme, a flat-type antenna is used as the antenna 16*a* and the antenna 51*a*, electric power is supplied from the reader writer 16 to the RF tag 5*b* using a radiation electromagnetic wave (a radio wave), and data is transferred from the RF tag 5*b* to the reader writer 16 by a reflected wave (a radio wave). In the radio wave scheme, since intensity attenuation is an inverse of a distance, longer distance communication is possible compared with the electromagnetic induction scheme. The access instrument 5 is configured to guide the insertion section 1*a* into the subject. The endoscope 1 includes a sensor configured to acquire the detection result when the insertion section 1*a* is inserted into the access instrument 5. The access instrument 5 includes the antenna 51*a* configured to transmit a radio wave or a magnetic field. The sensor includes the antenna 16*a*. The detection result is the radio wave or the magnetic field transmitted by the antenna 51*a* during inserting of the insertion section 1*a* into the access instrument 5.

Communication by the RFID is performed, for example, as explained below.

The control circuit 16*b* of the reader writer 16 transmits information on a radio wave or a magnetic field from the antenna 16*a* based on control of the endoscope controller 15.

The antenna 51*a* of the RF tag 5*b* receives the radio wave or the magnetic field from the reader writer 16.

Electric power is generated in the antenna 51*a* of the RF tag 5*b* by rectification (in the case of the radio wave) or resonance (in the case of the magnetic field).

The RF tag 5*b* causes the control circuit 51*b* and the memory 51*c* to operate with the generated electric power. The control circuit 51*b* transmits data in the memory 51*c* on a radio wave or a magnetic field from the antenna 51*a* of the RF tag 5*b*.

The reader writer 16 receives, with the antenna 16*a*, the radio wave or the magnetic field from the RF tag 5*b* and converts the radio wave or the magnetic field into an electric signal. The control circuit 16*b* of the reader writer 16 extracts information from the electric signal outputted from the antenna 16*a* and transmits the information to the endoscope controller 15.

In other words, in the present embodiment, as the event relating to the insertion of the insertion section 1*a* into the subject, an event in which the RF tag 5*b* has been detected based on the radio wave or the magnetic field received by the second antenna 16*a* is used. As the information concerning the detection result recorded in the endoscope memory 14, for example, history information (a "used" flag) indicating whether the endoscope 1 is unused or used is used. However, as in the first embodiment, the information is not limited to the "used" flag.

Action of the endoscope system using the RFID in the present embodiment is basically the same as the action explained with reference to FIG. 3 to FIG. 5.

Note that, as in the first embodiment, the main body controller 24 may detect an output of the reader writer 16 and rewrite the endoscope memory 14 according to a detection result.

According to such a second embodiment, substantially the same effects as the effects in the first embodiment explained above can be achieved by using the RFID. Since the RFID using the radio wave or the electromagnetic induction scheme (the magnetic field) in the present embodiment is the noncontact communication as in the first embodiment, the radio wave or the magnetic field can be detected even if a certain degree of a blocking object is present. There is an advantage that the configuration of the second embodiment is stain-resistant.

Third Embodiment

Figure 8:
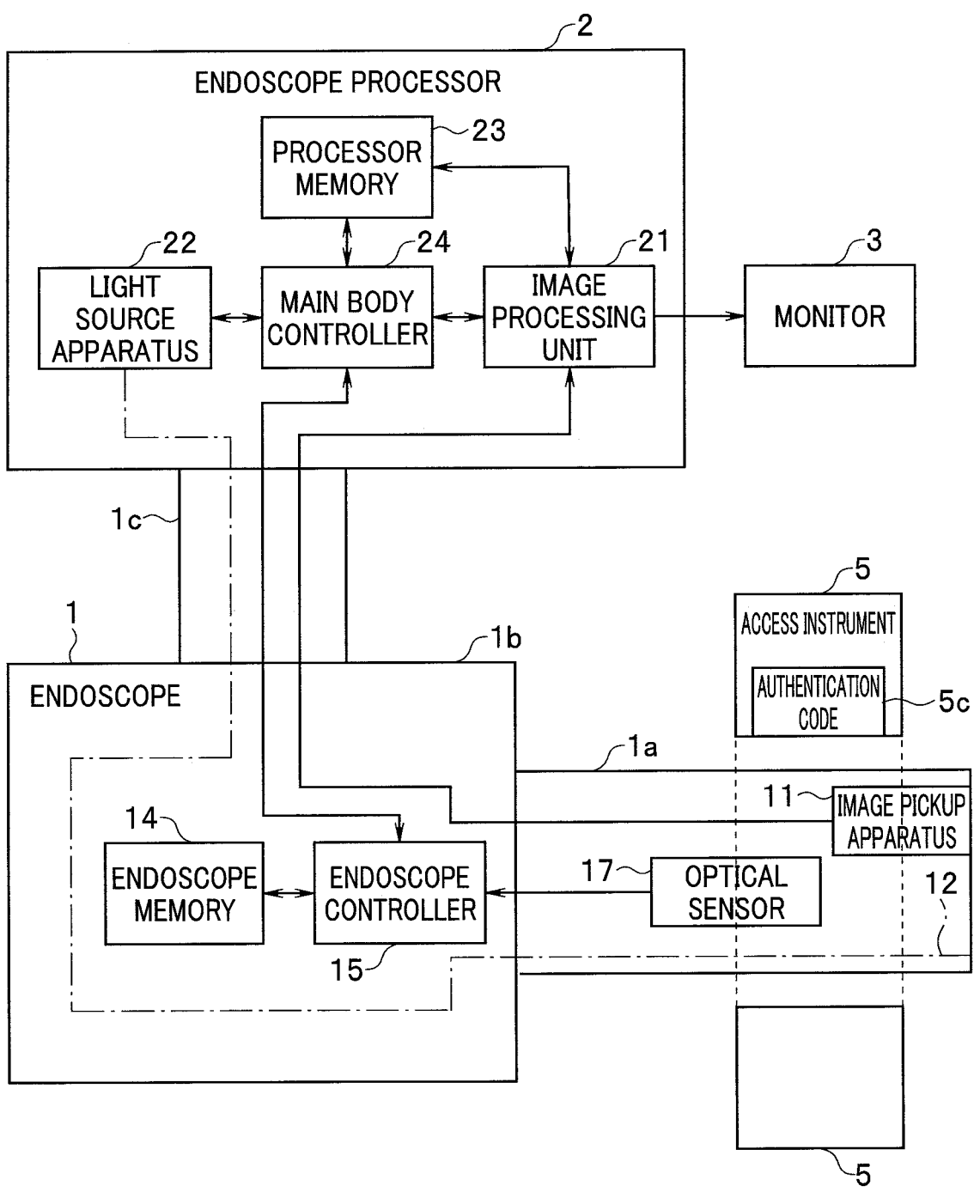
FIG. 8 is a block diagram mainly showing an electric configuration of an endoscope system in a third embodiment of the present disclosure.

FIG. 8 shows a third embodiment of the present disclosure and is a block diagram mainly showing an electric configuration of an endoscope system. In the third embodiment, the same portions as the portions in the first and second embodiments are denoted by the same reference numerals and signs and explanation of the portions is omitted as appropriate. Differences from the first and second embodiments are mainly explained.

In the third embodiment, the event relating to insertion of the insertion section 1*a* into the subject is detected using an authentication code 5*c* and an optical sensor 17 instead of the magnet 5*a* and the coil 13 in the first embodiment and the RF tag 5*b* and the reader writer 16 in the second embodiment.

In other words, the authentication code 5*c* is provided in the access instrument 5 and, in the insertion section 1*a* of the endoscope 1, the optical sensor 17 is provided as a sensor that acquires a result of detecting that the insertion section 1*a* has been inserted into the access instrument 5. The optical sensor 17 is connected to the endoscope controller 15. A setting place of the optical sensor 17 is not particularly limited if the setting place is in the insertion section 1*a*. However, for example, as in the first and second embodiments, the optical sensor 17 may be provided in a position of approximately 20 to 30 cm from the distal end face of the insertion section 1*a*. The other components of the endoscope system are substantially the same as the components shown in FIG. 2.

Specific examples of the authentication code 5*c* are a barcode, a two-dimensional barcode, and the like. However, the authentication code 5*c* is not limited to the barcode, the two-dimensional barcode, and the like. As the authentication code 5*c*, for example, a specific pattern may be used or a specific color may be used. The specific color may be a specific color of the access instrument 5 itself.

The authentication code 5*c* is provided on a surface of the access instrument 5. When the access instrument 5 is formed in a tubular shape like a mouthpiece or a trocar, the authentication code 5*c* may be provided on an inner circumferential surface of the access instrument 5.

In this way, in the present embodiment, as the event relating to the insertion of the insertion section 1*a* into the subject, an event in which illumination light has been radiated from an illumination apparatus and light reflected by the access instrument 5 (more specifically, light reflected by the authentication code 5*c*) has been detected is used. As information concerning the detection result recorded in the endoscope memory 14, for example, history information (a "used" flag) indicating whether the endoscope 1 is unused or used is used. However, as in the first and second embodiments, the information is not limited to the "used" flag. The access instrument 5 is configured to guide the insertion section 1*a* into the subject. The endoscope 1 includes a sensor configured to acquire the detection result when the insertion section 1*a* is inserted into the access instrument 5. The illumination apparatus is configured to radiate light from the insertion section 1*a*. The sensor includes an optical sensor 17, and the detection result is the light radiated by the illumination apparatus during inserting of the insertion section 1a into the access instrument 5. The access instrument 5 includes the authentication code 5c is configured to reflect the light radiated by the illumination apparatus, and the optical sensor 17 may be configured to detect the reflected light. The access instrument 5 includes the authentication code 5c is configured to absorb the light radiated by the illumination apparatus, and the optical sensor 17 may be configured to detect the reflected light from an area adjacent to the authentication code 5c.

Action of the endoscope system using the authentication code 5c and the optical sensor 17 in the present embodiment is basically the same as the action explained with reference to FIG. 3 to FIG. 5.

Note that, as in the first and second embodiments, the main body controller 24 may detect an output of the optical sensor 17 and rewrite the endoscope memory 14 according to a detection result.

According to such a third embodiment, substantially the same effects as the effects in the first and second embodiments explained above can be achieved by detecting, with the optical sensor 17 provided in the insertion section 1a, reflected light by the authentication code 5c of the light radiated from the illumination apparatus.

In a manufacturing process, it is easy to provide a barcode, a color, or the like in the access instrument 5. Therefore, it is possible to manufacture the access instrument 5 at a low price.

Fourth Embodiment

Figure 9:
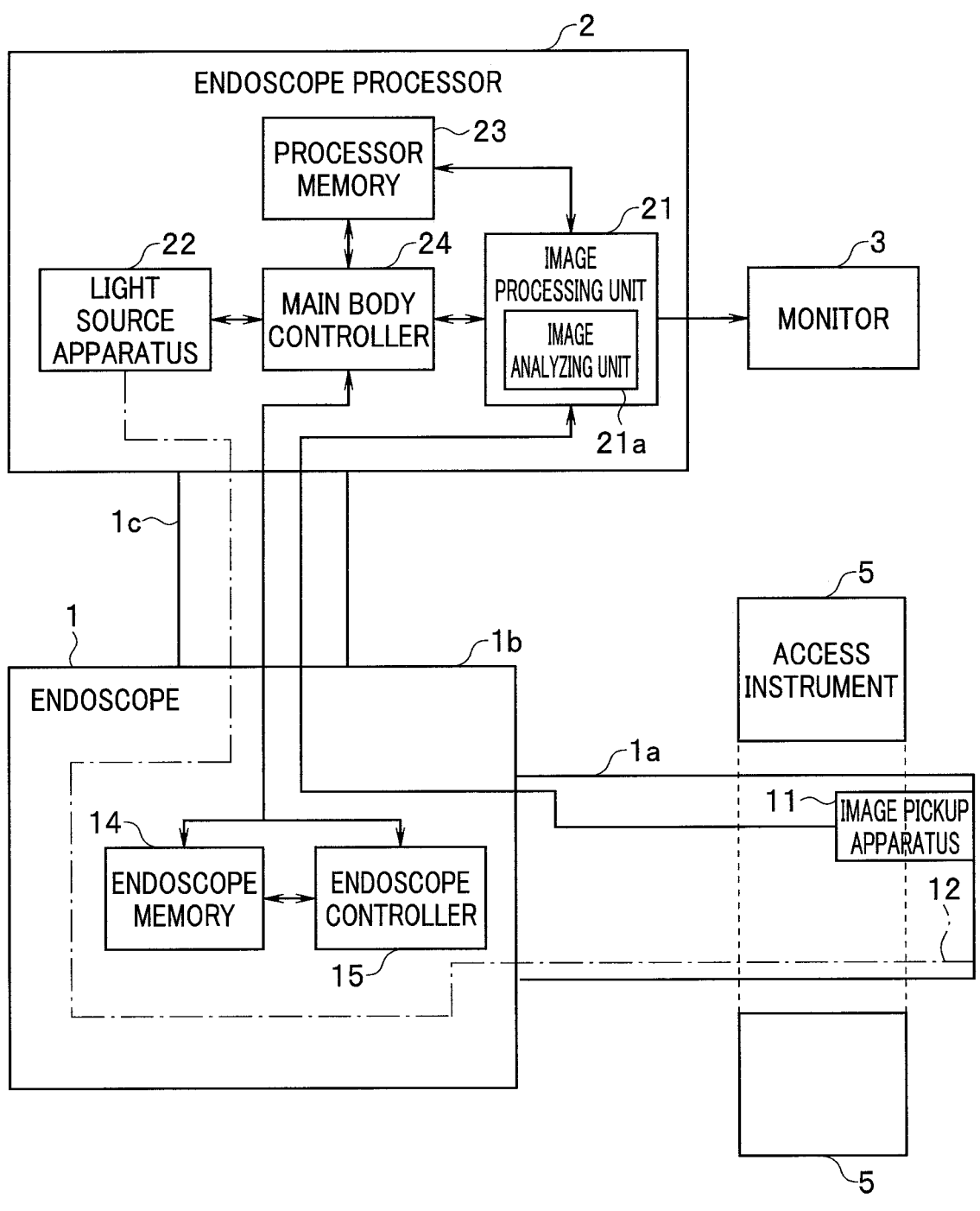
FIG. 9 is a block diagram mainly showing an electric configuration of an endoscope system in a fourth embodiment of the present disclosure.
Figure 10:
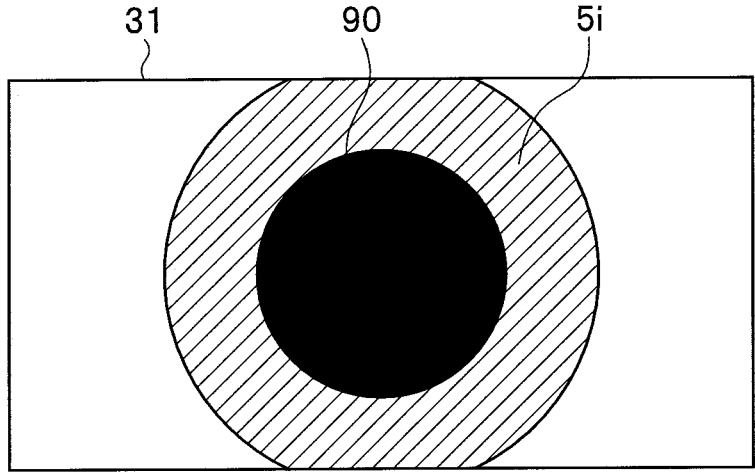
FIG. 10 is a diagram showing an example of an image at a time when an insertion section passes through an access instrument in the fourth embodiment.
Figure 11:
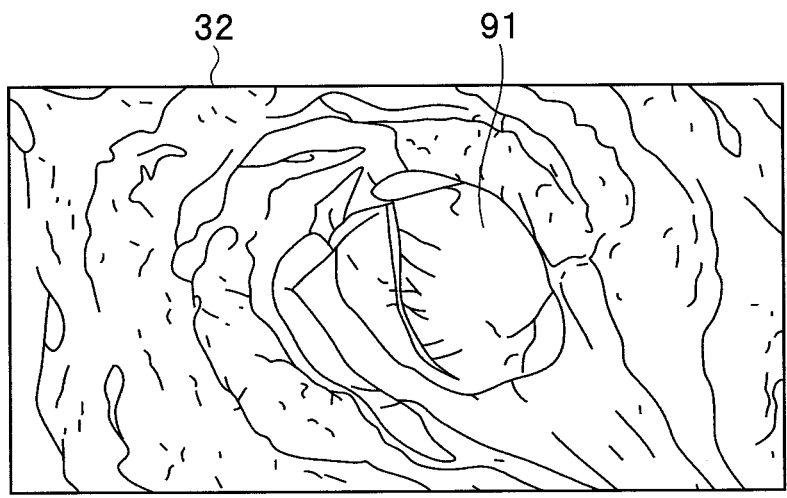
FIG. 11 is a diagram showing an example of an image at a time when the insertion section is present in a subject in the fourth embodiment.

FIG. 9 to FIG. 11 show a fourth embodiment of the present disclosure. FIG. 9 is a block diagram mainly showing an electric configuration of an endoscope system in the fourth embodiment. In the fourth embodiment, the same portions as the portions in the first to third embodiments are denoted by the same reference numerals and signs and explanation of the portions is omitted as appropriate. Differences from the first to third embodiments are mainly explained. The endoscope 1 includes the image pickup apparatus 11 configured to generate an image. Prior to recording of information, the endoscope 1 is configured not to supply power to the image pickup apparatus 11, and after recording of information, the endoscope 1 is configured to supply power to the image pickup apparatus 11.

In the first to third embodiments, the event relating to the insertion of the insertion section 1a into the subject is detected by detecting, with the sensor (the coil 13, the reader writer 16, or the optical sensor 17) provided in the endoscope 1, a specific component (the magnet 5a, the RF tag 5b, or the authentication code) of the access instrument 5. In contrast, in the present embodiment, an image picked up by the image pickup apparatus 11 provided in the insertion section 1a is analyzed to detect the event relating to the insertion of the insertion section 1a into the subject.

The image processing unit 21 that processes an image pickup signal generated by the image pickup apparatus 11 includes an image analyzing unit 21a. Note that the image analyzing unit 21a does not need to be provided in the image processing unit 21 and may be provided outside the image processing unit 21.

The image analyzing unit 21a is an image analyzing apparatus that analyzes, based on various kinds of information such as feature values such as a luminance, a color, and an edge component and a pattern of an image pickup signal or an image signal obtained by processing the image pickup signal, for example, whether an image is an image of an inside of the access instrument 5 or an image of an inside of the subject.

FIG. 10 is a diagram showing an example of an image 31 at a time when the insertion section 1a passes through the access instrument 5 in the fourth embodiment.

The image 31 at the time when the insertion section 1a passes through the access instrument 5 formed in the tubular shape includes an image portion 5i on the inner circumferential surface of the access instrument 5 where illumination light reaches and a certain degree of brightness is obtained and an image portion 90 in a dark part deeper than the access instrument 5 where the illumination light hardly reaches. The image analyzing unit 21a analyzes such features of the image 31 and outputs an analysis result to the main body controller 24. The main body controller 24 determines, based on the analysis result of the image analyzing unit 21a, whether the access instrument 5 has been detected. The endoscope processor 2 is configured to connect to the endoscope 1. The endoscope processor includes the main body controller 24 and the image analyzing unit 21a. The image analyzing unit 21a is configured to analyze the generated image as the detection result, and the main body controller 24 is configured to generate the information based on the analyzed generated image. The main body controller 24 may include the image analyzing unit 21a. And the endoscope controller 15 may be used as alternative of the main body controller 24.

In other words, in the example shown in FIG. 10, as the event relating to the insertion of the insertion section 1a into the subject, an event in which the image portion 5i on the inner circumferential surface of the access instrument 5 has been detected based on the analysis result of the image analyzing unit 21a is used.

Action of the endoscope system in a case in which the access instrument 5 is detected shown in FIG. 10 is basically the same as the action explained with reference to FIG. 3 to FIG. 5.

FIG. 11 is a diagram showing an example of an image 32 at a time when the insertion section 1a is present in a subject 91 in the fourth embodiment.

When the subject 91 is, for example, a lumen of an organism, the subject 91 has a specific complicated edge shape by a fold and a blood vessel and has a specific color balance, that is, for example, an amount of an R component is larger compared with a G component and a B component in an RGB color balance. The image analyzing unit 21a analyzes such features of the image 32 and outputs an analysis result to the main body controller 24. The main body controller 24 determines, based on the analysis result of the image analyzing unit 21a, whether an image in an inside of the subject 91 has been detected.

In other words, in the example shown in FIG. 11, as the event relating to the insertion of the insertion section 1a into the subject, an event in which an image of the inside of the subject 91 has been detected based on the analysis result of the image analyzing unit 21a is used.

Action of the endoscope system in a case in which an image of the inside of the subject 91 has been detected shown in FIG. 11 only has to replace, in FIG. 3 to FIG. 5, the determination about whether the access instrument 5 has been detected in step S4 with determination about whether an image of the inside of the subject 91 has been detected.

When determining that an image of the inside of the access instrument 5 or the subject 91 has been detected, the main body controller 24 rewrites the "used" flag of the endoscope memory 14 to a state in which the endoscope 1 is used.

As the information concerning to the detection result recorded in the endoscope memory 14, for example, history information (a "used" flag) indicating whether the endoscope 1 is unused or used is used. However, as in the first to third embodiments, the information is not limited to the "used" flag.

Note that, in the case of the example shown in FIG. 11 in which it is detected that the insertion section 1a has entered the inside of the subject 91 from an outside of the subject 91, the access instrument 5 may be absent. Therefore, the endoscope system in the present embodiment may not include the access instrument 5.

Since analysis processing by the image analyzing unit 21a has a relatively large processing load, the image analyzing unit 21a is provided in the endoscope processor 2 in the example shown in FIG. 9. Accordingly, the main body controller 24 rewrites the endoscope memory 14.

However, when the image analyzing unit 21a is provided in the endoscope 1, the endoscope controller 15 may rewrite the endoscope memory 14.

According to such a fourth embodiment, substantially the same effects as the effects in the first to third embodiments explained above can be achieved by performing the image analysis. In the case of the image analysis, it may not provide a magnet or the like in the access instrument 5 and it may not provide a separate sensor other than the image pickup apparatus 11 in the endoscope 1. Therefore, it is possible to reduce manufacturing cost of the access instrument 5 and the endoscope 1. The present embodiment can also be applied to an endoscope system that does not use the access instrument 5.

Fifth Embodiment

Figure 12:
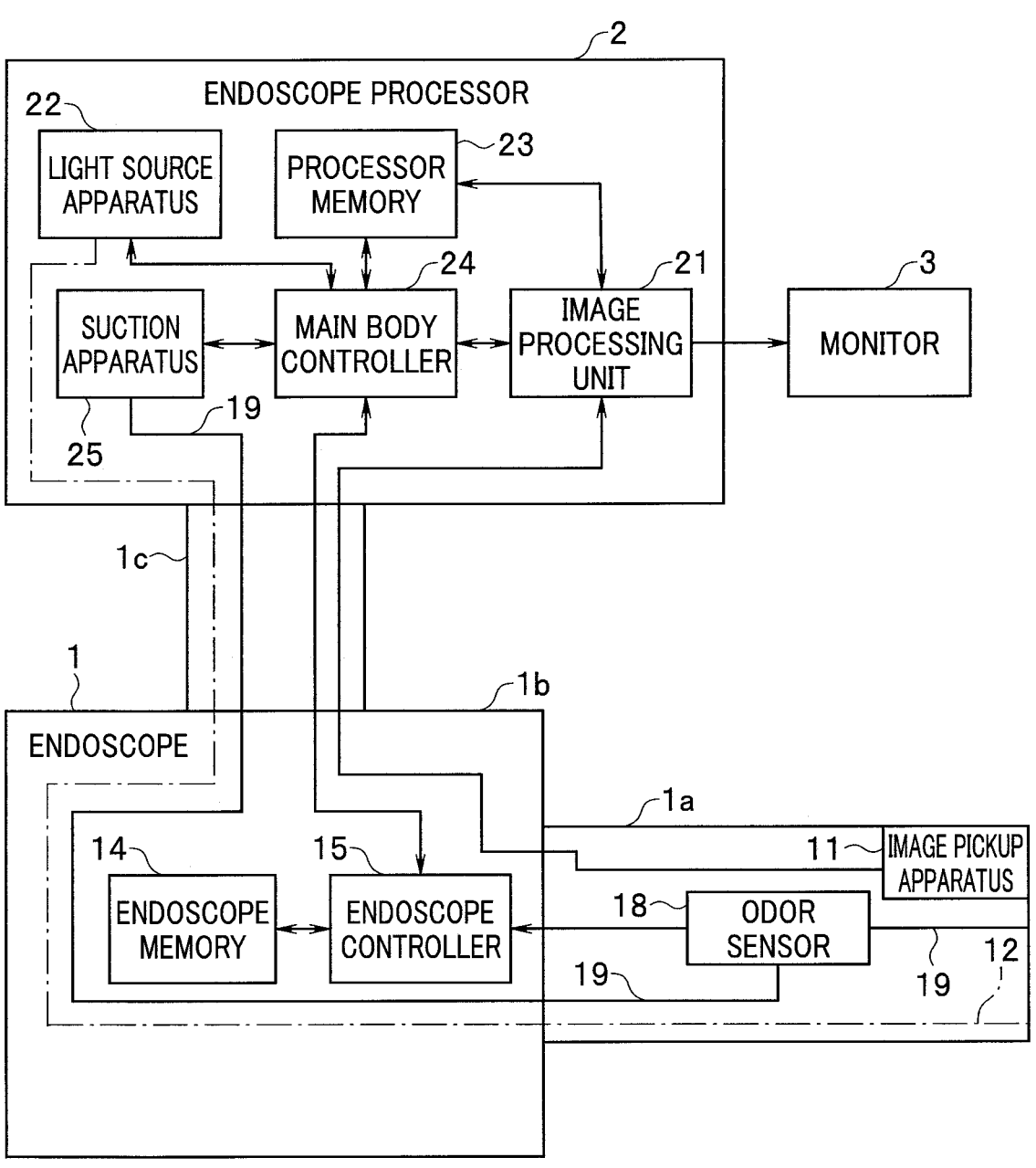
FIG. 12 is a block diagram mainly showing an electric configuration of an endoscope system in a fifth embodiment of the present disclosure.

FIG. 12 shows a fifth embodiment of the present disclosure and is a block diagram mainly showing an electric configuration of an endoscope system. In the fifth embodiment, the same portions as the portions in the first to fourth embodiments are denoted by the same reference numerals and signs and explanation of the portions is omitted as appropriate. Differences from the first to fourth embodiments are mainly explained.

In the present embodiment, an odor sensor 18 is used as a sensor that detects the event relating to the insertion of the insertion section 1a into the subject.

A part of a suction channel 19 is provided in the insertion section 1a, the operation section 1b, and the universal cord 1c of the endoscope 1.

A suction apparatus 25 and another part of the suction channel 19 connected to the suction apparatus 25 are provided in the endoscope processor 2. The suction channel 19 is configured to include the part of the suction channel 19 provided in the endoscope 1 and the other part of the suction channel 19 provided in the endoscope processor 2. Note that, here, an example is explained in which the endoscope processor 2 includes the suction apparatus 25. However, the suction apparatus 25 may be configured separately from the endoscope processor 2. The access instrument 5 is configured to guide the insertion section 1a into the subject. The endoscope 1 includes a sensor configured to acquire the detection result when the insertion section 1a is inserted into the access instrument 5. The endoscope system includes suction apparatus 25, the suction channel 19 connected to the suction apparatus 25 and configured to suction gas, the odor sensor 18 configured to detect an odor level as the detection result. The controller is configured to calculate a second detection result based on the detected odor level and a predetermined threshold.

When the connector 1c1 is connected to the endoscope processor 2, the suction channel 19 is connected to the suction apparatus 25 through the endoscope 1 and suctions gas from the inside of the subject.

The odor sensor 18 is provided on the suction channel 19 and detects an odor level of the gas passing in the suction channel 19. The odor sensor 18 outputs the detected odor level to the endoscope controller 15.

The odor sensor 18 detects an odor level of outside air until the insertion section 1a is inserted into the subject. The endoscope controller 15 records, for example, in the endoscope memory 14, the odor level of the outside air detected by the odor sensor 18. Note that, here, the odor level detected by the odor sensor 18 before the insertion section 1a is inserted into the subject is set as the odor level of the outside air. However, an odor level of air in an endoscopic examination room is assumed to be within a constant range. Therefore, a predetermined odor level may be set as the odor level of the outside air.

Thereafter, the insertion section 1a is inserted into the subject. When an inside of a lumen of the subject is observed in an endoscopic examination, in some case, air is fed into the lumen from an air feeding channel and the lumen is observed in a state in which the lumen is expanded. In this case, before the endoscope 1 is pulled out, the suction apparatus 25 is actuated to perform suction from a distal end of the suction channel 19 opened at the distal end portion 1a1 and release the air in the subject. At that time, the odor sensor 18 detects the gas suctioned through the suction channel 19, whereby an odor level of the inside of the subject is detected.

When the subject is an organism, odor levels are different in the outside air and the inside of the subject. In general, the odor level of the inside of the subject is higher than the odor level of the outside air. Therefore, the endoscope controller 15 calculates a difference between the odor level of the outside air recorded in the endoscope memory 14 and the odor level of the gas in the suction channel 19 detected by the odor sensor 18.

The endoscope controller 15 determines whether the calculated difference has exceeded a predetermined threshold. When determining that the difference has exceeded the predetermined threshold, the endoscope controller 15 estimates that the insertion section 1a has been inserted into the inside of the subject and rewrites the "used" flag of the endoscope memory 14 to a state in which the endoscope 1 is used.

In other words, in the present embodiment, as the event relating to the insertion of the insertion section 1a into the subject, an event in which the difference between the odor level of the outside air and the odor level of the gas in the suction channel 19 has exceeded the predetermined threshold is used. As the information concerning the detection result recorded in the endoscope memory 14, for example, history information (a "used" flag) indicating whether the endoscope 1 is unused or used is used. However, as in the first to fourth embodiments, the information is not limited to the "used" flag.

Action of the endoscope system shown in FIG. 12 only has to replace, in FIG. 3 to FIG. 5, the determination about whether the access instrument 5 has been detected in step S4 with determination about whether the difference between the odor levels has exceeded the predetermined threshold.

Note that, as in the first to third embodiments, the main body controller 24 may detect the output of the odor sensor 18 and rewrite the endoscope memory 14 according to a detection result.

In FIG. 12, an example is shown in which the odor sensor 18 is provided in the insertion section 1*a*. However, a setting place is not limited if the setting place is on the suction channel 19. Therefore, the odor sensor 18 may be provided in, for example, any of the operation section 1*b*, the universal cord 1*c*, and the connector 1*c*1. The odor sensor 18 may be provided on the suction channel 19 in the endoscope processor 2 or may be provided in the suction apparatus 25.

Note that, in the detection of the odor level by the odor sensor 18, the access instrument 5 may be absent. Therefore, the endoscope system in the present embodiment may not include the access instrument 5.

According to such a fifth embodiment, substantially the same effects as the effects in the first to fourth embodiments explained above can be achieved by detecting the odor level in the subject using the odor sensor 18.

In the case of the present embodiment, since it may not provide a magnet or the like in the access instrument 5, it is possible to reduce manufacturing cost of the access instrument 5. Further, the present embodiment can also be applied to an endoscope system that does not use the access instrument 5.

Note that, in the above explanation, a case in which the present disclosure is the endoscope system or the endoscope is mainly explained. However, the present disclosure is not limited to this and may be a control method for controlling the endoscope system or the endoscope as explained above or may be a computer program for causing a computer to perform the same processing as the processing of the endoscope system or the endoscope, a computer-readable non-transitory recording medium that records the computer program, and the like. The control method for the endoscope 1 including the insertion section 1*a* insertable into the subject. The control method comprises receiving the detection result relating to insertion of the insertion section 1*a* into the subject, and recording information indicating the detection result in the memory 14. The control method for the endoscope may comprise determining whether the information indicating the detection result is recorded in the memory 14, and permitting operation of the endoscope 1 when the information is not recorded, and prohibiting operation of the endoscope 1 when the information is recorded.

The present disclosure is not limited to the embodiments explained above per se. In an implementation stage, the constituent elements can be modified and embodied in a range not departing from the gist of the present disclosure. Aspects of various embodiments can be formed by appropriate combinations of a plurality of constituent elements disclosed in the embodiments. For example, several constituent elements may be deleted from all constituent elements explained in the embodiments. Further, constituent elements described in different embodiments may be combined as appropriate. In this way, it goes without saying that various modifications and applications are possible within a range not departing from the gist of the disclosure.

Example 1. An endoscope system comprising:
an endoscope including an insertion section inserted into a subject;
a memory; and
a controller configured to, when an event relating to insertion of the insertion section into the subject is detected, record information concerning a detection result in the memory.

Example 2. The endoscope system according to Example 1, wherein the controller determines whether the information concerning the detection result is recorded in the memory, permits use of the endoscope when the information is not recorded, and prohibits the use of the endoscope when the information is recorded.

Example 3. The endoscope system according to Example 1, wherein the memory is provided in the endoscope.

Example 4. The endoscope system according to Example 1, wherein the controller records, as the information concerning the detection result, in the memory, history information indicating that the endoscope is used.

Example 5. The endoscope system according to Example 1, further comprising:
an access instrument used when the insertion section is inserted into the subject, the insertion section being inserted into the access instrument; and
a sensor provided in the endoscope and configured to acquire a result of detecting that the insertion section is inserted into the access instrument, wherein the controller records information concerning the detection result by the sensor in the memory.

Example 6. The endoscope system according to Example 5, wherein
the access instrument includes a magnetic body that generates a magnetic field,
the sensor includes a coil provided in the insertion section, and
the controller records, in the memory, information concerning a result of detecting an electric current flowing from the coil when the coil moves relative to the magnetic body.

Example 7. The endoscope system according to Example 5, wherein
the access instrument includes a first antenna configured to transmit a radio wave or a magnetic field,
the sensor includes a second antenna provided in the insertion section and configured to receive the radio wave or the magnetic field, and
the controller records, in the memory, information concerning a result of detecting the radio wave or the magnetic field received by the second antenna.

Example 8. The endoscope system according to Example 5, further comprising an illumination apparatus configured to radiate light from the insertion section, wherein
the sensor includes an optical sensor provided in the insertion section, and
the controller detects recording of, in the memory, information concerning a result of detecting, with the optical sensor, the light radiated from the illumination apparatus and reflected by the access instrument.

Example 9. The endoscope system according to Example 8, wherein
the access instrument includes an authentication code, and
the optical sensor detects light reflected by the authentication code.

Example 10. The endoscope system according to Example 1, further comprising:
an image pickup apparatus provided in the insertion section, and
an image analyzing apparatus configured to analyze an image picked up by the image pickup apparatus, wherein
the controller detects, based on an analysis result of the image analyzing apparatus, an event relating to insertion of the insertion section into the subject.

Example 11. The endoscope system according to Example 10, further comprising a processor to which the endoscope is connected, wherein the controller and the image analyzing apparatus are provided in the processor, and the memory is provided in the endoscope.

Example 12. The endoscope system according to Example 1, further comprising:

a suction apparatus;

a suction channel connected to the suction apparatus through the endoscope and configured to suction gas from an inside of the subject; and an odor sensor provided on the suction channel, wherein the controller calculates a difference between an odor level of the gas in the suction channel detected by the odor sensor and an odor level of outside air and, when the difference exceeds a predetermined threshold, records, in the memory, information concerning a result of detecting that the difference exceeds the predetermined threshold.

Example 13. An endoscope comprising:

an insertion section inserted into a subject;

a sensor configured to detect an event relating to insertion of the insertion section into the subject;

a memory; and a controller configured to, when the event relating to the insertion is detected by the sensor, record information concerning a detection result in the memory.

Example 14. The endoscope according to Example 13, wherein the controller determines whether the information concerning the detection result is recorded in the memory, permits use of the endoscope when the information is not recorded, and prohibits the use of the endoscope when information is recorded.

Example 15. A control method for an endoscope, an insertion section of which is inserted into a subject, the control method for the endoscope comprising:

detecting, with a sensor, an event relating to insertion of the insertion section into the subject; and when the event relating to the insertion is detected by the sensor, recording information concerning a detection result in a memory.

Example 16. The control method for the endoscope according to Example 15, further comprising:

determining whether the information concerning the detection result is recorded in the memory, and permitting use of the endoscope when the information is not recorded and prohibiting the use of the endoscope when the information is recorded.

What is claimed is:

1. An endoscope system, comprising:

a controller configured to:

receive a detection result relating to insertion of an insertion section of an endoscope into a subject; and record information indicating use of the endoscope based on the detection result; and an access instrument configured to guide the insertion section, the access instrument including an authentication code, wherein the insertion section includes an image pickup apparatus configured to generate an image and an optical sensor, the optical sensor being arranged at a position of 20 cm or more from a distal end face of the insertion section toward a proximal end side, and wherein the optical sensor detects the authentication code, to acquire the detection result.

2. The endoscope system according to claim 1, wherein the controller is further configured to:

determine whether the information indicating use of the endoscope is recorded in a memory, permit operation of the endoscope when the information is not recorded, and prevent operation of the endoscope when the information is recorded.

3. The endoscope system according to claim 1, further comprising:

a memory configured to store the detection result.

4. The endoscope system according to claim 3, wherein the memory is located in the endoscope.

5. The endoscope system according to claim 3, wherein the controller is configured to record information indicating use of the endoscope based on the detection result received in the memory when the detection result is received twice.

6. The endoscope system according to claim 1, wherein, prior to recording of information, the endoscope is configured not to supply power to the image pickup apparatus, and wherein, after recording of information, the endoscope is configured to supply power to the image pickup apparatus.

7. The endoscope system according to claim 6, further comprising a processor configured to connect to the endoscope, wherein the processor includes the controller, and wherein the controller is configured to:

analyze the generated image as the detection result; and generate the information based on the analyzed generated image.

8. The endoscope system according to claim 1, wherein the access instrument includes a magnetic material configured to generate a magnetic field, wherein the sensor includes a coil, and wherein the detection result is an electric current in the coil occurring when the magnetic material moves relative to the coil during inserting of the insertion section into the access instrument.

9. The endoscope system according to claim 1, wherein the access instrument includes a first antenna configured to transmit a radio wave or a magnetic field, wherein the sensor includes a second antenna, and wherein the detection result is the radio wave or the magnetic field transmitted by the first antenna during inserting of the insertion section into the access instrument.

10. The endoscope system according to claim 1, further comprising an illumination apparatus configured to radiate light from the insertion section, wherein the detection result is the light radiated by the illumination apparatus during inserting of the insertion section into the access instrument.

11. The endoscope system according to claim 10, wherein the authentication code is configured to reflect the light radiated by the illumination apparatus, and wherein the optical sensor is configured to detect the reflected light.

12. The endoscope system according to claim 10, wherein the authentication code is configured to absorb the light radiated by the illumination apparatus, and wherein the optical sensor is configured to detect the reflected light from an area adjacent to the authentication code.

13. The endoscope system according to claim 1, further comprising:

a suction apparatus;

a suction channel connected to the suction apparatus and configured to suction gas; and an odor sensor configured to detect an odor level as the detection result, wherein the controller is configured to calculate a second detection result based on the detected odor level and a predetermined threshold.

14. The endoscope system according to claim 1, wherein the controller is configured to:

count time after receiving the detection result, and record information indicating use of the endoscope when the counted time is larger than a predetermined time.

15. The endoscope according to claim 1, wherein the authentication code is selected from the group consisting of a barcode, a two-dimensional barcode, a pattern and a color.

16. An endoscope, comprising:

an insertion section insertable into a subject;

an optical sensor configured to detect a detection result relating to insertion of the insertion section into the subject;

a memory; and a controller configured to:

receive the detected detection result; and record information indicating the detected detection result in the memory, wherein the insertion section includes an image pickup apparatus configured to generate an image and the optical sensor, the optical sensor being arranged at a position of 20 cm or more from a distal end face of the insertion section toward a proximal end side, and the optical sensor configured to detect an authentication code included with an access instrument configured to guide the insertion section, and wherein detecting the detection result includes the optical sensor detecting the authentication code.

17. The endoscope according to claim 16, wherein the controller is further configured to:

determine whether the information concerning the detected detection result is recorded in the memory, permit operation of the endoscope when the information is not recorded, and prevent operation of the endoscope when the information is recorded.

18. The endoscope according to claim 16, wherein the authentication code is selected from the group consisting of a barcode, a two-dimensional barcode, a pattern and a color.

* * * * *